Figure 1:
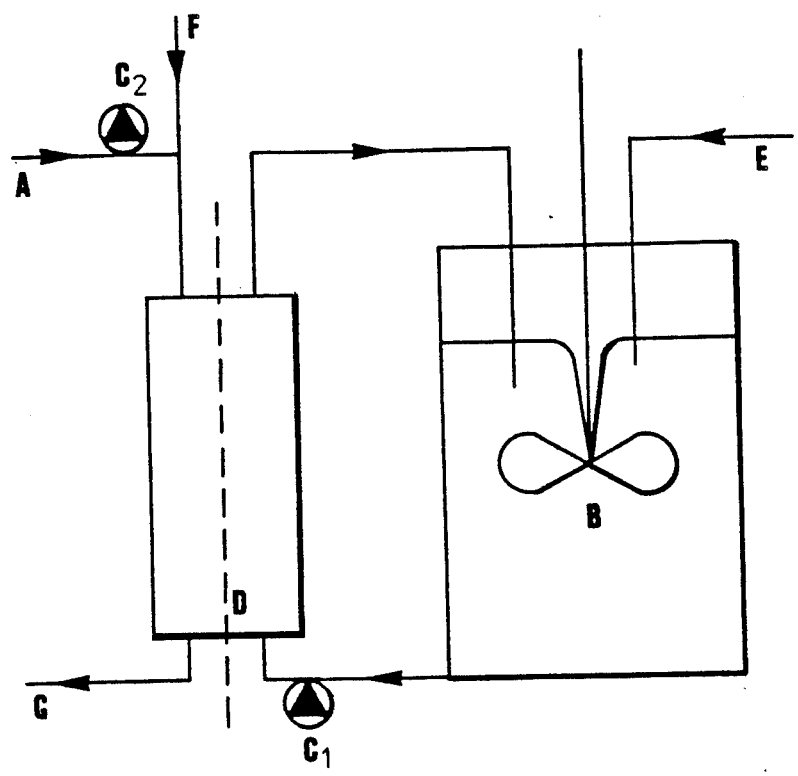

United States Patent [19]

Klaver et al.

[11] Patent Number: 4,938,973

[45] Date of Patent: Jul. 3, 1990

[54] PROCESS FOR PRODUCING FERMENTED MILK PRODUCTS

[75] Inventors: Franciscus A. M. Klaver; Fedde Kingma, both of Ede, Netherlands

[73] Assignee: Nederlands Instituut Voor Zuivelonderzoek, Ede, Netherlands

[21] Appl. No.: 276,814

[22] Filed: Nov. 28, 1988

[30] Foreign Application Priority Data

Dec. 14, 1987 [NL] Netherlands .......................... 8703019

[51] Int. Cl.$^5$ ................................................ A23C 9/12
[52] U.S. Cl. ........................................ 426/42; 426/43; 426/61; 426/580
[58] Field of Search ....................... 426/42, 43, 34, 61, 426/580, 38–40

[56] References Cited

FOREIGN PATENT DOCUMENTS

WO85/01064  3/1985  Int'l Pat. Institute .

OTHER PUBLICATIONS

"Improving the Flavor of Cultured Buttermilk", Cultured Dairy Products Journal, Aug., 1984, by Joseph F. Frank, pp. 6–9.

"Cultivation of Syntrophic Anaerobic Bacteria in Membrane-Separated Culture Devices", Chemical Abstracts, vol. 107, No. 9, Abstract No. 76063w, Aug. 1987, by M. Stieb et al., pages 561 and 562.

"How Yogurt Bacteria Co-operate During Their Growth", Netherlands Milk and Dairy Journal, vol. 37, No. 1/2, 1983, by F. Driessen et al., page 106.

"Production of Lactobacillus Cells by Dialysis Continous Fermentation of Deproteinized Whey", Journal of Dairy Science, vol. 63, 1980, by R. Stieber et al., pp. 722–730.

"Controlled Fermentation of Buttermilk", Cultured Dairy Products Journal, Mar. 1982, by E. Lundstedt et al., pp. 6–8.

"Yoghurt Made From Single Starter Organisms Using Heat- or Enzyme-Treated Milk or Milk to which Casein Hydrolysate or Sodium Formate is Added", Journal of Dairy Research, vol. 49, 1982, by V. Marshall et al., pp. 147–152.

Primary Examiner—Marianne Cintins
Attorney, Agent, or Firm—Young and Thompson

[57] ABSTRACT

Fermented milk products, such as yoghurt and buttermilk, are produced by fermentation of a suitable raw material, such as milk, with different microorganism species, in such a way that microorganisms that are beneficial in the production stage but unfavourably affect the product quality during storage, are kept apart from the fermentation mixture by means of a semipermeable membrane. The process can be carried out in a fed batch system or continuously, preferably with continous pH control. The products so obtained have improved taste and storage properties.

16 Claims, 3 Drawing Sheets

PROCESS FOR PRODUCING FERMENTED MILK PRODUCTS

The invention relates to a process for producing fermented milk products with the aid of two or more species of micro-organisms.

Fermented milk products are understood to mean the products which are produced by incubating milk or a raw material derived therefrom with particular micro-organisms. The raw material is often cows milk but the milk of other animals, such as buffalos, horses, sheep or goats can also be used, as can cream or whey. The milk may be whole milk, but also partially or completely skimmed milk; the dry substance content of the raw material is sometimes adjusted to the nature of the product to be produced.

Although a number of these products have formed an important component of the human diet in some regions since time immemorial, the dissemination has also increased considerably in recent decades, as has the number of product variations. Examples of products involved are yoghurt, sour cream and ymer. Buttermilk, which was formerly obtained exclusively as a by-product in the production of butter, is also at present often produced by allowing milk to acidify using specific microorganisms.

The microorganisms used in the production of fermented milk products are often mixtures of lactic acid bacteria which are termed starters.

A distinction is made between "single-strain starters", which consist of bacteria of one particular strain, "multiple-strain starters", which consist of a few particular strains, and "mixed-strain starters", which consist of an undefined number of different strains of different species of lactic acid bacteria.

In Western Europe, "mixed-strain starters" are generally used; these can often be obtained commercially in the form of concentrates. In this connection a distinction is made (XVIth Int. Dairy Congress, 1962, Vol. D, 143-167) between the following types of cultures:

O starters consisting of strains of *Streptococcus cremoris* and *Streptococcus lactis;*

B starters consisting of strains of *Streptococcus cremoris, Streptococcus lactis, Leuconostoc cremoris* and *Leuconostoc lactis;*

D starters consisting of strains of *Streptococcus cremoris, Streptococcus lactis* and *Streptococcus diacetilactis* (also described as *Streptococcus lactis, var. diacetilactis*);

BD starters consisting of strains of *Streptococcus cremoris, Streptococcus lactis, Streptococcus diacetilactis, Leuconostoc cremoris* and *Leuconostoc lactis.*

Although all the said species of lactic acid bacteria convert lactose into lactic acid, *S. lactis* and *S. cremoris* are eminently suitable for the purpose; the other species mentioned are primarily of importance in forming other substances which contribute to the organoleptic properties, such as diacetyl and carbon dioxide.

The abovementioned lactic acid bacteria species are of the mesophilic type, that is to say said bacteria are capable of growth at temperatures between approximately 18° C. and approximately 30° C.

On the other hand, thermophilic species of bacteria are also used in the production of certain fermented milk products: bacteria which are capable of growing in the temperature range between approximately 30° and approximately 45° C.

For the production of yoghurt use is made of (thermophilic) starters consisting of strains of *Lactobacillus bulgaricus* and *Streptococcus thermophilus.* An interaction (protocooperation) which is not essential for growth but does benefit both species occurs in milk between these two species. This finds expression, for example, in the more rapid formation of acid by the mixed culture than by the separate pure cultures. During growth, the bacteria of each species produce compounds which the other species is able to use and which are present in milk only to a small extent.

The nature of the product is determined to a considerable extent by the microorganisms used because, depending on the species or strain, they contribute to a greater or lesser extent to the formation of acid such as lactic acid, of other flavouring substances such as diacetyl or acetaldehyde, of gas such as carbon dioxide, and of structure-forming constituents such as polysaccharides.

In some cases, one particular species of bacteria is used, such as *L. acidophilus* in the production of acidophilus milk, but usually the product acquires its characteristic properties as a consequence of the action of a mixture of species of microorganisms on the raw material. A very complicated example is found in kefir: in the so-called kefir tubercles acetic acid bacteria and various yeasts are detected in addition to lactobacilli and streptococci.

A problem in the case of fermented milk products is that a rapid deterioration of the taste of the product often occurs during the storage after production as a consequence of the presence of an organism used in the production.

Thus, in the case of buttermilk, a considerable drop in the content of diacetyl, an extremely important flavouring component in this product, occurs during storage. Buttermilk is at present generally produced by fermenting milk with B or BD starters. The *Leuconostoc* strains and possibly *S. diacetilactis* strains present in these starters are primarily of importance as a result of the production of diacetyl from citrate. It has been found (Cult. Dairy Prod. J. 19 (3) (1984) 6) that one of the most important reasons for the disappearance of diacetyl is the enzyme diacetyl reductase, an enzyme which is present, inter alia, in bacteria of many strains of precisely those species of bacteria which are used as diacetyl producers in the production of buttermilk.

An attempt has been made to solve this problem by aerating the fresh product (NIZO report NOV. 1192 (1986)); it was found, however, that this process results in poorly reproducible results: sometimes the drop in diacetyl content during storage was in fact reduced, but in other cases a marked drop occurred despite the aeration.

Another example of a product whose taste is adversely affected during storage by a microorganism which is used in the production is yoghurt. This product is produced in many forms, but use is always made of a mixture of *S. thermophilus* and *L. bulgaricus.* The streptococcus produces formic acid essential for the growth of the lactobacillus, while the lactobacillus releases some amino acids which are indispensible for the streptococcus, including threonine, which can be converted into the flavouring component acetaldehyde by the action of the streptococcus. The quality of the final product is, however, adversely affected during storage by the presence of the lactobacillus, which not only plays a part in the acidification proceeding too far (Milchwissenschaft 35 (1980), 470–473), but may eventually also cause the defect "sharpness" as a result of proteolysis. It has been demonstrated that *S. thermophilus* is in fact capable in principle of producing yoghurt flavour even without the aid of *L. bulgaricus*, but only if the milk has undergone a pretreatment with specific enzymes or if specific additives (casein hydrolysates) are present in the milk (J. Dairy Res. 49 (1982), 147).

It has been found that problems such as those described in the abovementioned cases in which a microorganism essential for the production of a fermented milk product adversely affects the quality of the final product during storage can be avoided by using the process according to the invention. This process for producing fermented milk products is characterized in that microorganisms that have an unfavourable effect on the quality of the product during storage but are beneficial for the production thereof are kept apart from the fermentation mixture from which the product is produced by means of a semipermeable membrane in a membrane fermenter.

Where the products concerned are always produced in the known processes by inoculating the starting liquid with a mixture containing all the species of microorganisms required, the process according to the invention avoids the final product containing those organisms which may affect the quality adversely, while substances produced by said organisms are nevertheless able to permeate the culture liquid which is being converted into product. In order to achieve this, use may be made of a membrane fermenter.

The raw material for the fermentation may be milk or a substance derived therefrom. Milk is preferably used.

A membrane fermenter is a vessel in which microbiological processes can be allowed to proceed while the contents can be fed past a semipermeable membrane. A liquid in which compounds up to a certain size, depending on the molecular cut-off value of the membrane, can be taken up from the fermentation vessel, can be fed past the other side of the membrane. Thus, a required reaction product can be taken up in water on the other side of the membrane from the fermentation mixture and, if required, isolated therefrom. It is also possible to remove via the membrane a metabolite which inhibits the growth of the organisms in the fermenter in order to increase the yield of microorganisms in this manner. If it is required for the action of the different microorganisms, a different temperature can be maintained on either side of the membrane.

The membrane used in said fermenters is generally a membrane of the hollow fibre type. The molecular cut-off value is in general between $10^3$ and $10^6$ Dalton; in order to achieve an exchange of low-molecular weight compounds only, a less open membrane will be chosen than if it is required to retain only relatively large particles such as bacteria.

If it is required to produce a fermented milk product in a continuous process, use may be made, for example, of a fermenter as shown diagrammatically in FIG. 1. The microorganisms to be kept apart from the product are kept in compartment B; there are facilities for stirring the contents of B, for adding substances via line E, and for causing the contents to circulate past the membrane D by means of pump $C_1$.

After inoculation with the other microorganisms required and, if necessary, after adding other substances via line F, the raw material may be pumped with the aid of pump $C_2$ via line A past the membrane, via which membrane the culture liquid is able to take up the required substances produced by the microorganism in B. The product or, if the production process also involves subsequent stages, such as further acidification, the intermediate product, can be drained off at G.

Figure 2:
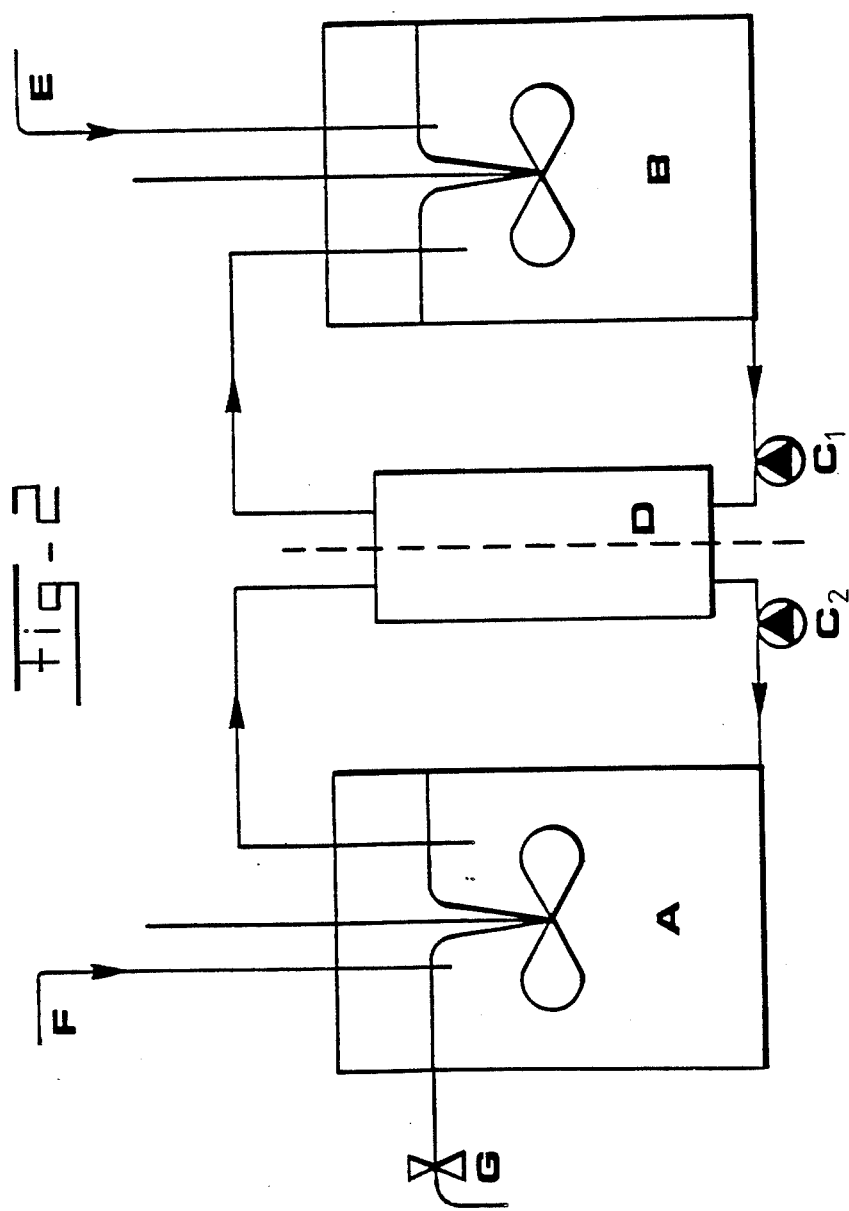

A fermenter as shown diagrammatically in FIG. 2 is suitable for a batchwise production of a fermented milk product. In this type of fermenter, too, the microorganisms to be kept apart from the product are kept in compartment B; the product or the intermediate product is cultured in compartment A. Pump $C_2$ can be used to cause the contents of A to circulate past the membrane. This type can, however, also be used in a continuous process by continuously adding raw material to A and discharging excess culture liquid via tap G. The drained-off portion may then undergo, if necessary, a further treatment in a continuous process or per batch.

The fermentation will generally be allowed to proceed until a particular pH value at which the production in B of the required substances is optimum is reached. The pH in the membrane fermenter should not, however, become less than approximately 5.0 because the proteins present in the fermentation raw material will otherwise coagulate and block up the membrane. If the pH approaches the critical value for the coagulation of the proteins and it is still required to continue the fermentation in order to improve the organoleptic properties of the product, the pH is consequently preferably kept at a value between 6.0 and 5.1. This can be done in a known manner by means of continuously or periodically adding neutralizing agent. Equipment for automatically maintaining the set pH value is known.

Advantageously, unacidified raw material, such as milk, may be added as neutralizing agent to compartment A; more usual agents such as ammonium hydroxide, calcium hydroxide, sodium hydroxide, potassium hydroxide, sodium carbonate, calcium carbonate, phosphates and organic ammonium hydroxides can also be used for maintaining the set pH value. Preferably, the fermentation raw material is used for neutralizing.

If required the product obtained in the production section of the membrane fermenter can be allowed to acidify further after discontinuing the exchange via the membrane or after removal from the fermenter.

The principle of the fermenter shown in FIG. 2 is suitable, in particular, for carrying out the process according to the invention as a "fed-batch" system, for example in the production of buttermilk or yoghurt. The "fed-batch" system is a particular form of a chargewise production, which is preferred. In this case, the chosen pH value is maintained by adding milk, but no intermediate product is drained off. Once a required quantity of intermediate product containing sufficient substances which have diffused out of B through the membrane has been obtained, A is shut off from access to the membrane and the intermediate product in A is allowed to acidify further. After the acidification, the product, which is still in compartment A, undergoes, if necessary, further operations such as stirring or aeration; finally, the finished product is drained off from A. When designed as a "fed-batch" system, a compartment A which is large compared with B is used.

Thus, according to the invention, for example, buttermilk can be produced by culturing, in the fermenter shown in FIG. 2, lactic acid bacteria in compartment A which do not contain any diacetyl reductase but do not produce any diacetyl either, and by keeping in B flavour producers which ferment citrate (*Leuconostoc* species and/or *S. diacetilactis*). The substrate in B may be milk, but also another source of citrate such as ultrafiltration permeate from cheese whey. In the last-mentioned case, in which there will be virtually no question of any growth, the number of citrate-fermenting microorganisms should already be sufficiently high immediately after inoculation: sufficient material is used for inoculation that the number of citrate-fermenting bacteria is, for example, $10^8$ to $10^9$ per ml of culture liquid. If milk is used as the medium in B, an inoculation such that the abovementioned number is reached after a growth period of, for example, 15 hours may be adequate. If required, other substances such as citrate may be added. Adding citrate is primarily beneficial in the case of prolonged fermentation.

Exchange of components of the media in the two compartments may take place when the culture liquids are each circulated past one side of the membrane if the size of said substances is below the molecular cut-off value of the membrane used. It is beneficial to maintain the pH of the culture liquid at a particular value before and during circulation, which value lies between limits which are determined, on the one hand, by possible contamination of the membrane by precipitated protein and, on the other hand, by the need for an adequate citrate conversion. Preferably, pH value is adjusted to between 5.2 and 5.6.

During culturing, the temperature of the culture liquid is kept at a constant value which, in the case of buttermilk production, is preferably between 17° C. and 26° C.

Culturing can be carried out both batchwise and continuously. In the latter case, milk is used as neutralizing agent in compartment A, and the excess culturing liquid is drained off from A in a manner such that the volume of the liquid remaining in A remains on average the same during the production period.

The drained-off portion is kept at the set culturing temperature until the pH reaches a value below 4.8, preferably a value of 4.6. Then the product may be considered to be ready; it is kept preferably at 7° C. until the moment of consumption.

It has been found that, just as in the case of the product produced in the known manner, the diacetyl content of the product obtained with the aid of the fermenter decreases during storage. It is consequently beneficial to gas the finished product with oxygen or air: in that case, in contrast to the diacetyl content of the normal buttermilk gassed with oxygen, the diacetyl content of the product according to the invention remains stable during storage; it even exhibits the tendency to increase somewhat.

A diacetyl content in the finished product of approximately 3 to 6 mg per kg is to be preferred organoleptically.

Another possible application of the process according to the invention is the production of yoghurt. For this purpose, thermophilic streptococci are cultured in milk in compartment A of the fermenter shown diagrammatically in FIG. 2, while *L. bulgaricus* is cultured in B. Milk, but also, for example, cheese whey ultrafiltration permeate enriched with milk protein, can be used as substrate for the lactobacillus.

Culturing is carried out preferably at a temperature between 31° and 46° C., as is normal in the known methods of yoghurt production. During culturing, the contents of A and those of B are circulated by pumping past the membrane. Preferably, the pH is maintained at a value between 5.2 and 6.0. Like the buttermilk production described earlier, this yoghurt production can also be carried out batchwise or as a continuous process. If carried out as a continuous process, milk is added to A as a neutralizing agent and the excess culture liquid (intermediate product) is drained off via G. After being drained off, said intermediate product is kept at the culturing temperature until the pH has reached a value below 4.6; the finished product is kept at, for example, 7° C. It is then found that although the intermediate product drained off from A acidifies more rapidly than a culture of the *S. thermophilus* strain used in milk, it does so more slowly and to a lesser extent than a mixture of the *S. thermophilus* and *L. bulgaricus* strains used in milk.

The acetaldehyde content, which is 1 to 2 mg/kg in the case of a completely acidified culture of *S. thermophilus* in milk, reaches values of 7 mg/kg or above in the final product of the process according to the invention.

The yoghurt production can also be carried out as a "fedbatch" system.

The invention is illustrated by means of the following examples. A membrane fermenter as shown diagrammatically in FIG. 2 was used. The membrane was composed of hollow cellulose acetate fibres, type C-DAK 90 SCE, molecular cut-off value 10,000 Dalton (CD-Medical Inc.). Both compartments were provided with an electrode, which is not shown in FIG. 2, which made automatic pH regulation possible. The entire system was kept under a slight overpressure of sterile nitrogen gas.

Where mention is made of gassing in the examples, it is meant that oxygen gas was passed through the liquid to be treated for a short time until the oxygen concentration was 9 mg per liter and the liquid was then kept at 20° C. for 1 hour.

The determination of the diacetyl content was carried out as described in Neth. Milk Dairy J. 38 (1984), 251–263; citrate was determined by the Deniges method as described in Neth. Milk Dairy J. 15 (1961) 127–150. Quantities of acetaldehyde were determined as described in Neth. Milk Dairy J. 24 (1970), 34–44.

The bacteria strains *Lactobacillus bulgaricus Ib* and *Streptococcus thermophilus Sts* used in the examples have been deposited under numbers 903.87 and 904.87 respectively at the Centraal Bureau voor Schimmelcultures (Central Office for Mould Cultures) in Baarn. The cultures used in the examples, BD starter A, O starter Fr48Z1, D starter 4/25 and yoghurt starter I St are obtainable from the CSK (Coöperatieve Stremsel- en Kleurselfabriek) in Leeuwarden.

EXAMPLE I

A fermented milk product was produced in a membrane fermenter. For this purpose, the compartments A and B were each filled with 2 kg of milk which was heated beforehand at 85° C. for 5 minutes. The milk in A was inoculated with 1% (m/m) of the O starter Fr48Z1; the milk in B was inoculated with 1% (m/m) of the D starter 4/25. Both batches were circulated by pumping, in countercurrent, at 20° C. When the pH of the milk had reached the value of 5.4, said value was then maintained by an addition, controlled by a pH meter, of 7M ammonia solution.

When, after circulating by pumping for 16 hours, it was no longer possible to detect citrate, the product was drained off from A. One portion of the product was gassed, but not the other portion. The product was kept at 7° C. The diacetyl content was determined at set times. The results, expressed in mg/kg, are stated in Table A.

TABLE A

| Storage time (days at 7° C.) | Diacetyl in the product (mg/kg) | |
|---|---|---|
| | without gassing | with gassing |
| 0 | 3.0 | 3.3 |
| 5 | 1.7 | 3.5 |
| 11 | 1.3 | 3.5 |

EXAMPLE II

The production described in Example I was repeated, with the proviso that the milk was inoculated with the BD starter A in compartment A. The results of the diacetyl determination are shown in Table B.

TABLE B

| Storage time (days at 7° C.) | Diacetyl in the product (mg/kg) | |
|---|---|---|
| | without gassing | with gassing |
| 0 | 1.6 | 3.2 |
| 5 | 1.2 | 2.7 |
| 9 | 0.9 | 3.1 |

EXAMPLE III

Buttermilk was prepared in a membrane fermenter as shown in FIG. 2. For this purpose, 2 kg of skimmed milk was introduced into compartment A which had been heated at 85° C. for 5 minutes beforehand. This milk was inoculated with 1% (m/m) of the O starter Fr48Z1 and then incubated at 20° C. When the pH of the milk had reached a value of 5.4, this value was maintained by an addition, controlled by a pH meter, of pasteurized skimmed milk; the volume in A was kept constant by allowing the excess to drain off. There was no circulation by pumping.

Almost 16 hours after the milk in A had been inoculated, compartment B was provided with 2 kg of sterilized cheese whey ultrafiltration permeate (5% m/m dry substance); the pH of this permeate was brought to the value of 5.4 before sterilization with the aid of 7M NaOH solution and was kept at this value during the buttermilk production by an addition, controlled by a pH meter, of a $Ca(OH)_2$ suspension.

The buttermilk production was started 16 hours after inoculating the milk by inoculating the permeate with a concentrate of D culture 4/25, and by starting the circulation by pumping milk and permeate past the membrane. The quantity of culture concentrate was chosen so that the number of bacilli in the permeate was approximately $10 \times 10^7$ CFU of S. diacetilactis per ml.

The production was continued for 32 hours. During said production, the milk (the "intermediate product") flowed out of tap G at a virtually constant rate of approximately 0.7 kg.h-1; the intermediate product was collected in batches. The diacetyl content of the fresh intermediate product was determined at set times. The batches of intermediate product collected were further incubated at 20° C. until the pH thereof had reached the value of 4.6. The product thus obtained was then stored, in part without gassing and in part after gassing, for 10 days at 7° C., after which the diacetyl content was measured again. The results of the diacetyl determinations are summarized in Table C.

TABLE C

| | Diacetyl content (mg/kg) in intermediate product and in product | | | | |
|---|---|---|---|---|---|
| Hours after "start" | intermediate product (a) | product (fresh) | | product (after 10 days at 7° C.) | |
| | | (a) | (b) | (a) | (b) |
| 0 | 0.4 | | | | |
| 3.5 | 1.6 | | | | |
| 4 | | 2.0 | | 1.4 | 8.0 |
| 5 | | | 3.6 | | |
| 11.5 | 5.0 | | | | |
| 19.5 | 4.0 | | | | |
| 21.5 | | | | | |
| 22 | | 4.0 | | 2.6 | 12.1 |
| 23 | | | 5.8 | | |
| 25.5 | 3.3 | | | | |
| 30.5 | 2.6 | | | | |

(a): not gassed
(b): gassed

From the data in Table C it emerges that diacetyl can be detected in the intermediate product during the entire production period. After reaching the pH value of 4.6, the diacetyl content was found to have risen to the level of the diacetyl content of fresh buttermilk produced in a normal manner; the structure and taste were also comparable. If the product was stored without gassing, the diacetyl content was found to decrease; after the gassed product had been stored, the diacetyl content was found to have risen still further.

EXAMPLE IV

The buttermilk production described in Example III was repeated, with the proviso that the pH value was kept at 5.2 during the circulation by pumping and the initial volume both of the milk and of the permeate was 1.7 kg. 0.5 kg of intermediate product flowed out of tap G per hour.

In the case of this production, too, diacetyl was always found to detectable in the intermediate product during the production continued for 25 hours, albeit that the level was found to be lower than in the production described in Example III: 1.1 to 2.5 mg/kg in the intermediate product.

EXAMPLE V

Yoghurt was produced in a membrane fermenter as shown diagrammatically in FIG. 2. In compartment A, 1200 ml of skimmed milk (sterilized by heating for 2 s at 140° C. and degassed to less than 1 mg of oxygen per kg) was inoculated with 2.5% (m/m) of S. thermophilus strain Sts (CBS 904.87). During culturing at 45° C., a mixture of $N_2$ and $CO_2$ (95:5, v/v) was passed through the culture liquid. After the pH had reached the value of 5.7, this was maintained by adding sterilized skimmed milk; the volume in A was kept constant by allowing the excess to drain off via tap G. The liquid was stirred, but was not pumped past the membrane.

In compartment B, 5 liters of sterilized skimmed milk were inoculated with 2.5% (m/m) of L. bulgaricus strain Ib (CBS 903.87). Culturing was carried out at 45° C. while stirring but without circulating by pumping, with the gas mixture also passed through compartment A being passed through; the pH value of 5.7 was maintained by adding 7M ammonium hydroxide.

After the culture liquid had been kept for 39 hours at pH 5.7 in A and B separately, the culturing was continued for 7 hours with pumps switched on so that the liquids were in contact with each other via the membrane for this period. The acetaldehyde content in A was found to increase from 1.5 to rather more than 6 mg/kg in this period. This content increased to 7 mg/kg when the liquid in A was subsequently incubated separately for a further 16 hours.

EXAMPLE VI

In a fermenter as shown diagrammatically in FIG. 2, *S. thermophilus* strain Sts was cultured in compartment A and *L. bulgaricus* strain Ib in compartment B, in sterilized (2 s; 140° C.), degassed skimmed milk at 45° C. with a mixture of $N_2$ and $CO_2$ (95:5, v/v) being passed through. The volume of skimmed milk before inoculation was 1000 ml in both compartments, the inoculation percentage was 2.5% (m/m) in both cases. Both liquids were circulated past the membrane by pumping from the instant of inoculation. Said circulation by pumping was discontinued after approximately 3 hours, when the pH had reached the value of 5.7. The fermentation mixture was then further incubated in A without contact with the membrane.

Figure 3:
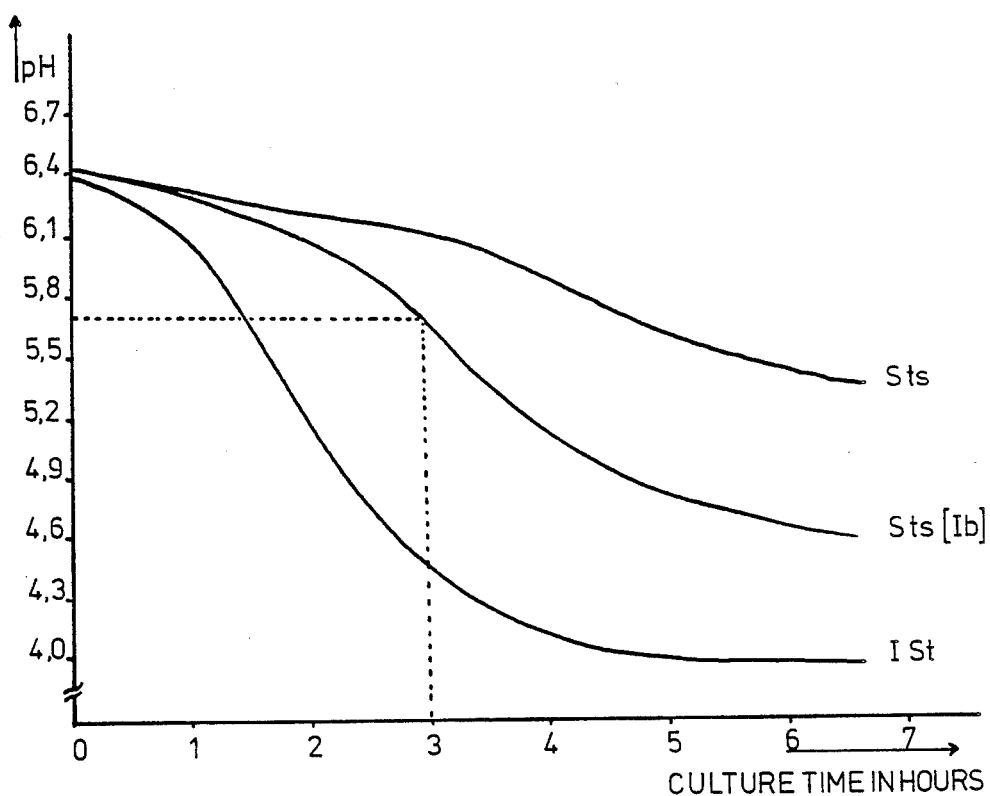

The variation of the pH in the product compartment A is shown in FIG. 3 by the line Sts[Ib]. The same figure shows the variation of the pH of a culture of Sts in skimmed milk (line Sts) and that of the pH of a culture of a normal yoghurt culture I St (line I St). The culturing temperature and the inoculation percentage were the same in the three cases.

We claim:

1. Process for producing fermented milk products comprising fermenting a raw milk material with two or more species of microorganisms in a membrane fermenter wherein during fermentation and subsequent storage, the microorganisms that degrade product quality during storage but are beneficial for product production are kept apart from the fermenting raw milk material by a semipermeable membrane in a membrane fermenter.

2. Process according to claim 1, wherein milk is used as fermentation raw material.

3. Process according to claim 1, wherein the pH is so regulated during the fermentation in the membrane fermenter that no coagulation occurs in the fermentation mixture.

4. Process according to claim 3, wherein, after the pH has reached a value in the range of 6.0–5.1, the pH is maintained at a value in said range.

5. Process according to claim 3, wherein the pH is regulated by adding fermentation raw material.

6. Process according to claim 5, wherein the process is carried out as a fed-batch system.

7. Process according to claim 5, wherein the process is carried out as a continuous process.

8. Process according to claim 1, wherein, after the fermentation in the membrane fermenter, the fermentation mixture is allowed to acidify further without exchange of substances via a membrane.

9. Process according to claim 1, wherein the microorganisms are citrate-fermenting streptococcaceae.

10. Process according to claim 9, wherein, after fermentation, the product is treated with oxygen.

11. Process according to claim 9, wherein citrate is added to the medium for the citrate-fermenting streptococcacea.

12. Process according to claim 9, wherein cheese whey ultrafiltration permeate is used as a medium for the citrate-fermenting streptococcaceae.

13. Process according to claim 9, wherein the fermentation temperature is kept at a value between 17° and 26° C.

14. Process according to claim 1, wherein the microorganisms apart are *Lactobacillus* species and a culture of *Streptococcus thermophilus* is in the product.

15. Process according to claim 14, wherein the fermentation temperature is kept at a value between 30° and 46° C.

16. Fermented milk product produced according to claim 1, said product being substantially free of diacetyl reductase-containing microorganisms.

* * * * *